United States Patent
Johnson

Patent Number: 5,819,571
Date of Patent: Oct. 13, 1998

[54] APPARATUS FOR BENDING SURGICAL INSTRUMENTS

[76] Inventor: Stephen Johnson, 1441 Avocado Ave., Suite 206, Newport Beach, Calif. 92660

[21] Appl. No.: 798,452

[22] Filed: Feb. 10, 1997

[51] Int. Cl.⁶ ..................................................... B21D 7/06
[52] U.S. Cl. ........................... 72/31.05; 72/31.12; 72/319
[58] Field of Search ............................... 72/319–321, 388, 72/217, 31.05, 31.12, 461; 163/1, 5

[56] References Cited

U.S. PATENT DOCUMENTS

| | | |
|---|---|---|
| D. 357,313 | 4/1995 | Wortrich . |
| 1,391,365 | 9/1921 | Carlson . |
| 1,868,852 | 7/1932 | Schneider ................................. 72/319 |
| 1,879,868 | 9/1932 | Breer . |
| 2,080,095 | 5/1937 | Sachleben . |
| 2,175,679 | 10/1939 | Beatty ...................................... 72/321 |
| 2,229,929 | 1/1941 | Morton et al. . |
| 2,396,619 | 1/1946 | Strayer . |
| 2,455,138 | 11/1948 | Perkins . |
| 2,464,800 | 7/1949 | Franck . |
| 2,927,490 | 3/1960 | Klamm . |
| 2,955,495 | 10/1960 | Stirling . |
| 3,004,583 | 10/1961 | Zuccala .................................... 72/31.12 |
| 3,194,038 | 7/1965 | Small ....................................... 72/319 |
| 3,538,737 | 11/1970 | Del Monica ............................. 72/319 |
| 3,540,112 | 11/1970 | Knox . |
| 3,808,867 | 5/1974 | Becker ..................................... 72/31.12 |
| 3,926,028 | 12/1975 | Kowal ...................................... 72/319 |
| 4,052,881 | 10/1977 | Mount ..................................... 72/31.05 |
| 4,169,984 | 10/1979 | Parisi . |
| 4,578,980 | 4/1986 | Beckman ................................. 72/319 |
| 4,785,650 | 11/1988 | Lusty ....................................... 72/321 |
| 5,222,937 | 6/1993 | Kagawa . |
| 5,263,950 | 11/1993 | L'Esperance, Jr. . |
| 5,351,518 | 10/1994 | Bogart et al. . |
| 5,403,307 | 4/1995 | Zelman . |
| 5,403,323 | 4/1995 | Smith . |
| 5,413,556 | 5/1995 | Whittingham . |
| 5,417,654 | 5/1995 | Kelman . |
| 5,433,013 | 7/1995 | Woodhouse . |
| 5,433,702 | 7/1995 | Zelman et al. . |

FOREIGN PATENT DOCUMENTS

| | | | |
|---|---|---|---|
| 19157 | of 1897 | United Kingdom ................... 72/319 |
| 355161 | 8/1931 | United Kingdom ................... 72/319 |

*Primary Examiner*—Daniel C. Crane
*Attorney, Agent, or Firm*—Blakely Sokoloff Taylor & Zafman

[57] ABSTRACT

An apparatus that allows a surgeon to bend a surgical instrument such as a phaco-emulsification tip at a surgical site. The apparatus includes a clamp that is mounted to a housing. The clamp may hold a proximal end of a phaco-emulsification tip. The tip is held adjacent to a die that is also attached to the housing. The surgeon can manually actuate an anvil that bends the phaco tip about the die. The distal end of the tip is bent along a scale located on the housing. The scale provides a visual indication of the bend angle of the tip. The surgeon can move the anvil until the distal end of the tip is aligned with a desired bend angle indicia of the scale. Multiple bend angles can be created in the phaco tip by rotating the tip within the clamp and re-actuating the anvil. The tip is eventually removed from the apparatus and attached to an ultrasonic handpiece for use in a phaco-emulsification procedure.

5 Claims, 3 Drawing Sheets

APPARATUS FOR BENDING SURGICAL INSTRUMENTS

BACKGROUND OF THE INVENTION

1. Field of the Invention

The present invention relates to an apparatus that allows a surgeon to bend a phaco-emulsification tip at a surgical site.

2. Description of Related Art

Cataracteous lenses are typically removed in a procedure commonly referred to as phaco-emulsification. Phaco procedures are performed by inserting an ultrasonically driven tip into the capsular bag of a cornea. The tip breaks up the lens through a combination of cutting and fluid cavitation within the eye. The lens fragments are then aspirated through an inner aspiration channel of the tip.

The phaco tips are typically bent to improve the maneuverability and cavitation efficiency of the phaco system. By way of example, U.S. Pat. No. 4,169,984 issued to Parisi, and U.S. Pat. No. 5,417,654 issued to Kelman and assigned to Alcon Laboratories, Inc., disclose phaco tips that are bent at the distal end.

The phaco tips are bent at a manufacturing facility remote from the surgical site. The tips may be bent by pressing a straight needle into a curved die as described and shown in U.S. Pat. No. 5,351,518 issued to Bogart et al.

Phaco tip manufacturers typically provide tips in a number of standard bend angles. To obtain a non-standard bend angle, the surgeon must submit a special purchase order to the manufacturer. The manufacturer then constructs a die to produce the specified angle. Such a procedure is time consuming and expensive. Additionally, bending the tip at the manufacturing facility does not allow the surgeon to adjust the bend angle at the surgical site. It would therefore be desirable to provide an apparatus that would allow the surgeon to bend a phaco-emulsification tip at the surgical site. It would also be desirable to provide an apparatus and method that would allow the surgeon to create multiple bend angles in a phaco-emulsification tip.

SUMMARY OF THE INVENTION

The present invention is an apparatus that allows a surgeon to bend a surgical instrument such as a phaco-emulsification tip at a surgical site. The apparatus includes a clamp that is mounted to a housing. The clamp may hold a proximal end of a phaco-emulsification tip. The tip is held adjacent to a die that is also attached to the housing. The surgeon can manually actuate an anvil that bends the phaco tip about the die. The distal end of the tip is bent along a scale located on the housing. The scale provides a visual indication of the bend angle of the tip. The surgeon can move the anvil until the distal end of the tip is aligned with a desired bend angle indicia of the scale. Multiple bend angles can be created in the phaco tip by rotating the tip within the clamp and re-actuating the anvil. The tip is eventually removed from the apparatus and attached to an ultrasonic handpiece for use in a phaco-emulsification procedure.

DETAILED DESCRIPTION OF THE INVENTION

Figure 1:
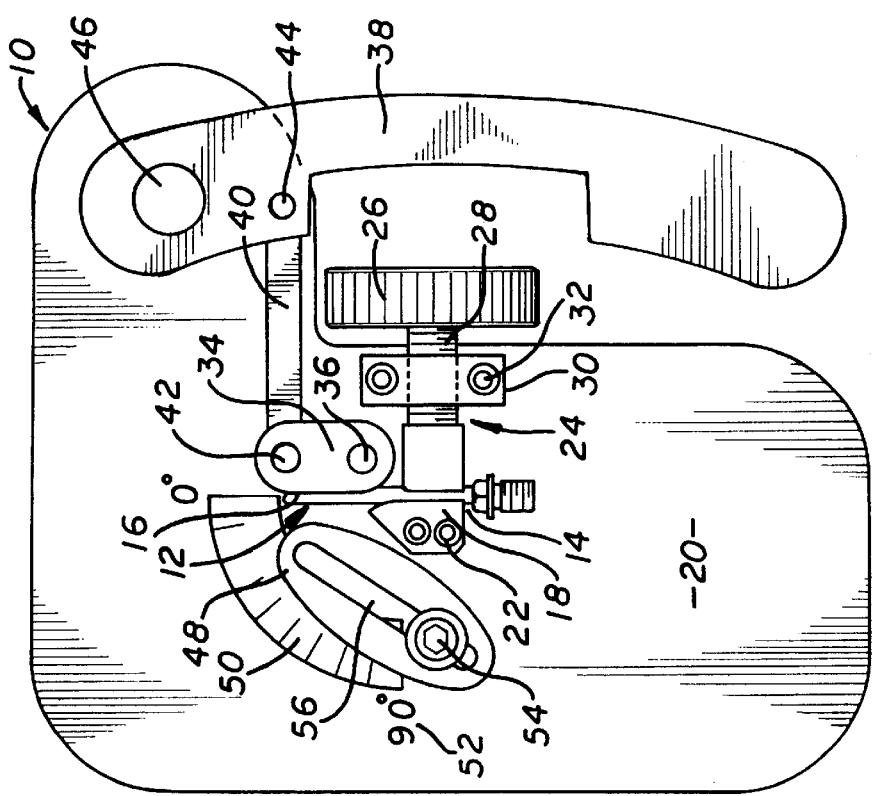
FIG. 1 is a side view of a phaco-emulsification tip bending apparatus of the present invention.

Referring to the drawings more particularly by reference numbers, FIG. 1 shows an apparatus 10 that bends a phaco-emulsification tip 12. The phaco tip 12 has a proximal end 14 and a distal end 16. The phaco tip 12 also has an inner aspiration channel (not shown) extending along the longitudinal axis of the tip 12. The apparatus 10 is relatively small in size and allows a surgeon to bend the tip 12 at a surgical site. The components of the apparatus 10 are preferably constructed from, and/or coated with, a corrosion resistant material to reduce the probability of contamination at the surgical site.

The apparatus 10 includes a die 18 that is mounted to a housing 20 by a pair of fasteners 22. The phaco-emulsification tip 12 is held by a clamp 24. The clamp 24 has a knob 26 and a threaded shank 28 that cooperates with a threaded plate 30 mounted to the housing 16 by fasteners 32. The knob 26 can be manipulated by the surgeon to move the clamp 24 relative to the die 18. Movement of the clamp 24 can either secure or disengage the tip 12 from the apparatus 10.

The apparatus 10 further includes an anvil 34 that is pivotally connected to the housing 20 by a pin 36. The anvil 34 is coupled to a handle 38 by a linkage bar 40 and pins 42 and 44. The handle 38 is pivotally connected to the housing 20 by pin 46. Rotation of the handle 38 pushes the anvil 34 and bends the distal end 16 of the phaco tip 12 about the die 18. The die 18 preferably has a curved working surface to minimize the stress point on the tip 12.

The anvil 34 can move until the tip 12 engages a stop 48. The distal end 16 of the tip 12 moves along a scale 50 which has a plurality of indicia 52. The indicia 52 provide a visual indication of the bend angle of the tip 12. The stop 48 is attached to the housing 20 by a screw 54 which extends through slot 56. The position of the stop 48 can be adjusted to vary the bend angle of the tip 12.

Figure 2:
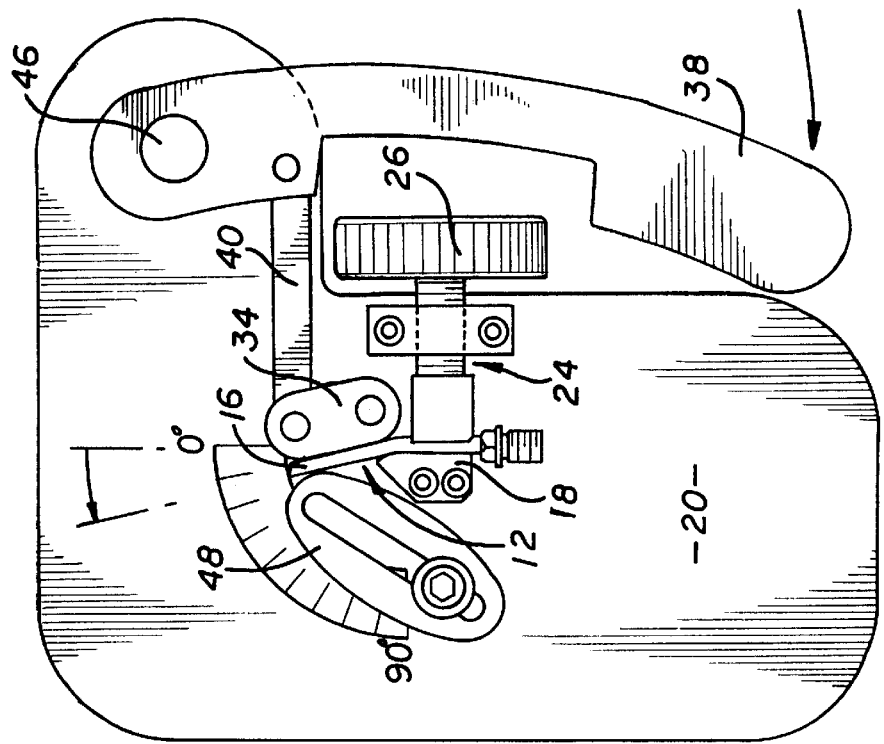
FIG. 2 is a side view showing a phaco-emulsification tip being bent by the apparatus.

In operation, the surgeon clamps the proximal end 14 of the tip 12 between the clamp 24 and the die 18. As shown in FIG. 2, the handle 38 is then rotated to actuate the anvil 34 and bend the tip 12 about the die 18. The anvil 34 moves the tip 12 until the distal end 14 engages the stop 48. The handle 38 is then pulled back to disengage the anvil 34. The apparatus 10 may have a spring (not shown) which pushes the handle 38 back to the original position. The knob 26 is eventually rotated to release the tip 12 from the apparatus 10.

To create a compound bend, the phaco tip 12 can be moved relative to the die 18, clamped in place, and then bent by re-actuating the anvil 34. By way of example, the phaco tip 12 may be rotated about its longitudinal axis and then bent to create a tip 12 that bends in different directions. The stop 48 may also be adjusted to vary the bend angle of the second curvature.

Figure 3:
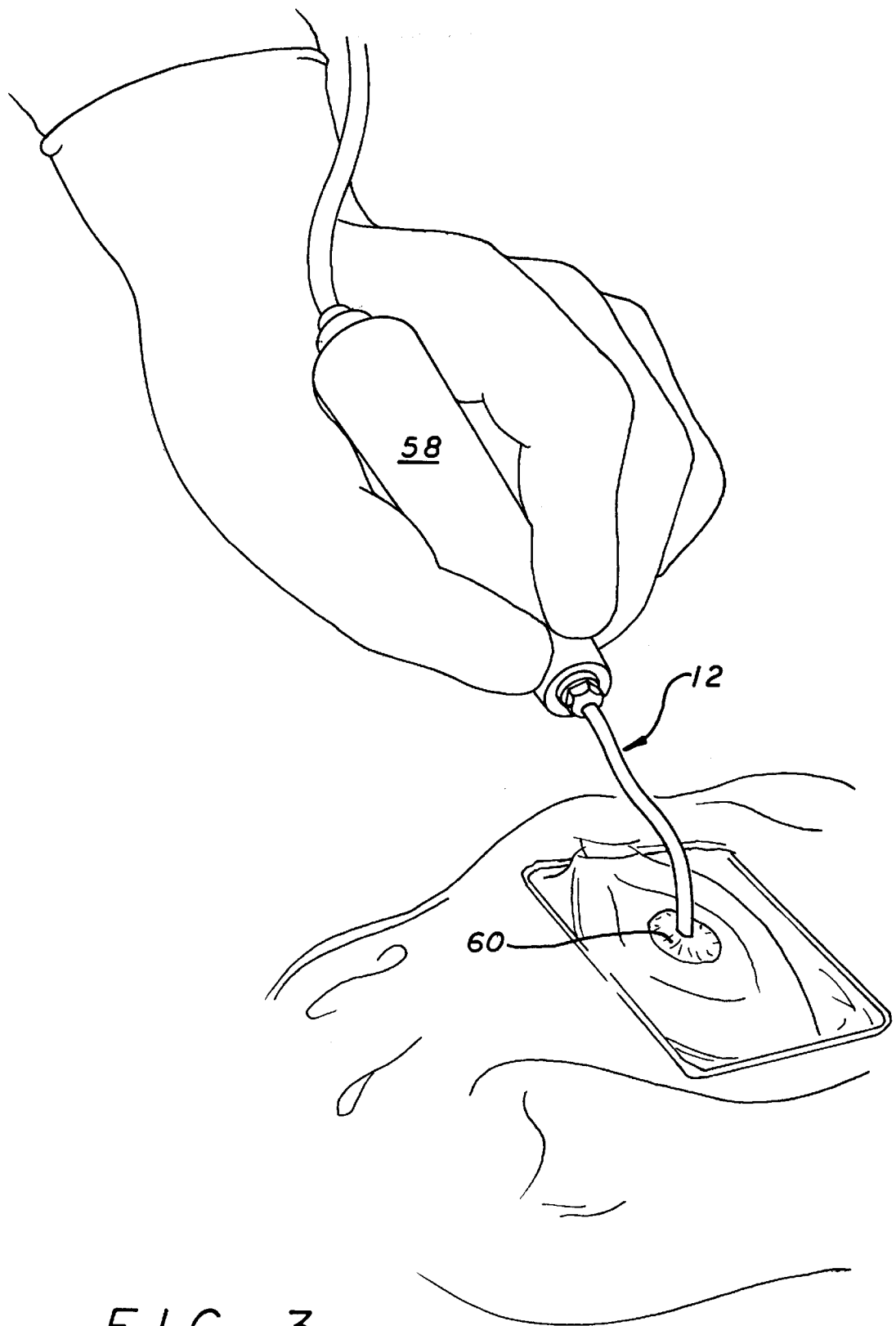
FIG. 3 is a perspective view showing a bent phaco-emulsification tip attached to an ultrasonic handpiece and inserted into the cornea of a patient.

After bending is complete the phaco tip 12 is removed from the apparatus 10 and attached to an ultrasonic handpiece 58 as shown in FIG. 3. The bent tip 12 can be inserted into a cornea 60 of a patient to perform a phaco-emulsification procedure. The surgeon may remove the phaco tip 12 from the patient and further bend the tip 12 with the apparatus 10. The apparatus 10 thus provides the surgeon with the ability to adjust the bend angle of the tip 12 during a procedure.

Figure 4:
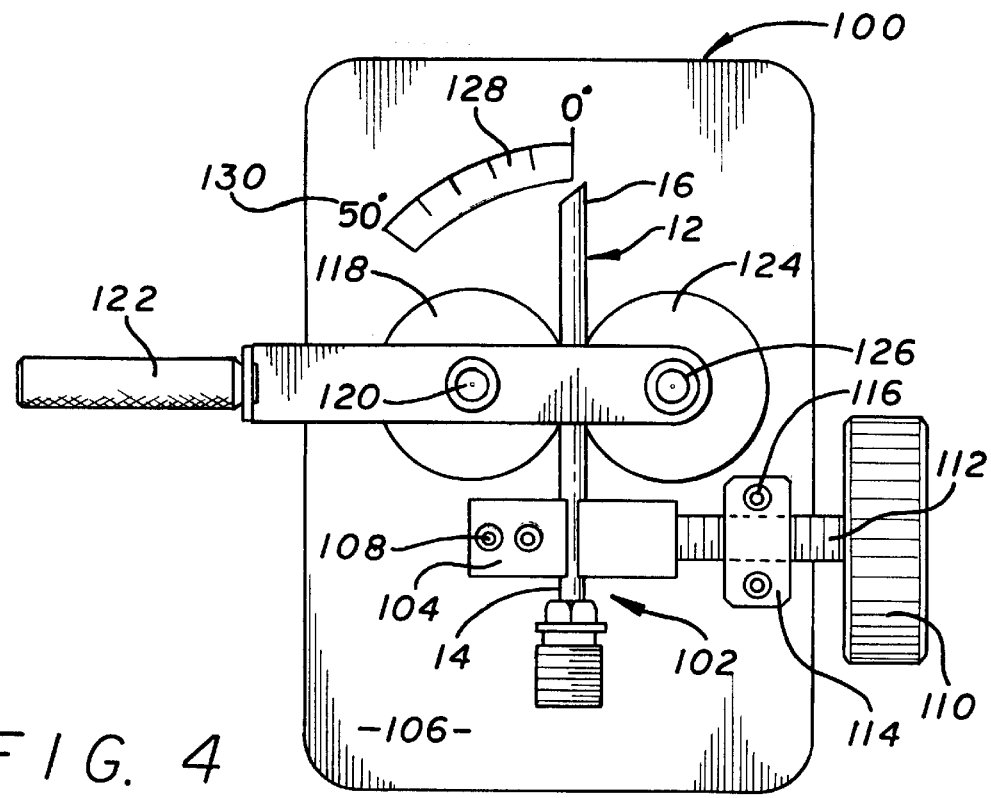
FIG. 4 is a side view showing an alternate embodiment of the apparatus.

FIG. 4 shows an alternate embodiment of an apparatus 100. The apparatus 100 includes a clamp 102 that presses the proximal end 14 of a tip 12 into a fixture plate 104 that is mounted to a housing 106 by fasteners 108. The clamp 102 has a knob 110, and a threaded shank 112 which cooperates with a threaded plate 114 that is mounted to the housing 106 by fasteners 116. A die wheel 118 is mounted to the housing 106 by a pin 120.

Pivotally connected to the pin 120 is a handle 122 that can be rotated by the surgeon. An anvil wheel 124 is pivotally connected to the end of the handle 122 by a pin 126. The housing 106 also has a scale 128 with angular indicia 130.

Figure 5:
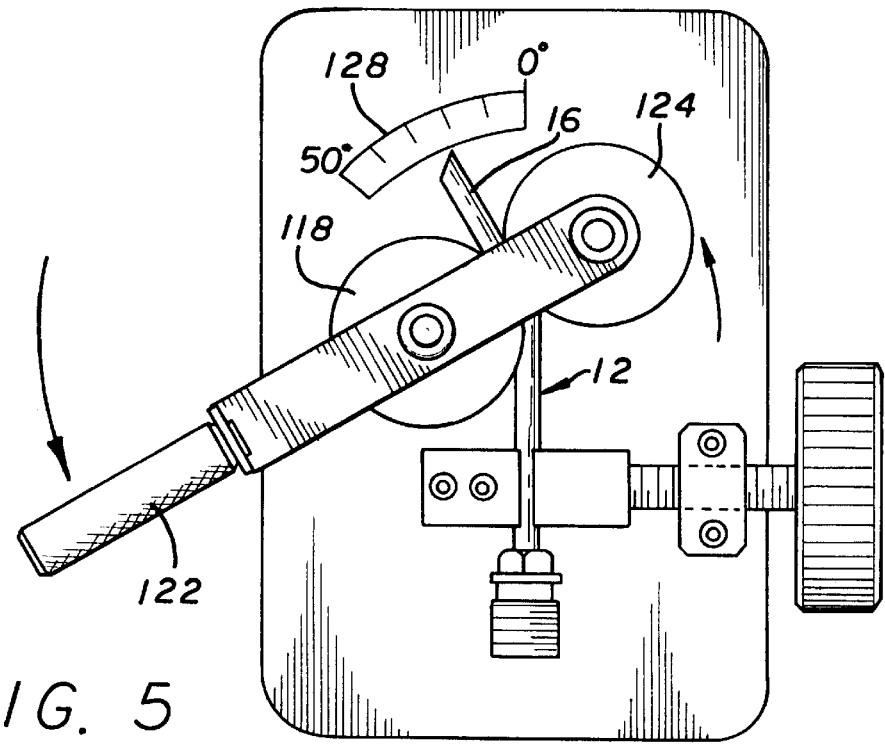
FIG. 5 is a side view showing a phaco-emulsification tip being bent by the apparatus shown in FIG. 4.

As shown in FIG. 5, in operation the surgeon rotates the handle 122 so that the anvil wheel 124 bends the tip 12 about the die wheel 118. The surgeon can rotate the handle 122 until the distal end 16 of the tip 12 is aligned with a desired angular indicia of the scale 128. The phaco tip 12 can be unclamped and moved within the apparatus 100 to create compound curvatures in the tip 12. The tip 12 is eventually removed from the apparatus 100 and assembled to an ultrasonic handpiece 58. Although not shown, the embodiment depicted in FIGS. 4 and 5 may also have the stop 48 shown in FIGS. 1 and 2.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art. For example, although bending a phaco-emulsification tip is described and shown, it is to be understood that the apparatus can be used to bend other surgical instruments at the surgical site, and away from the surgical site.

What is claimed is:

1. An apparatus that allows an operator to bend a surgical instrument, comprising:

a housing;

a scale located on said housing;

a clamp that is mounted to said housing and holds the surgical instrument;

an anvil that is coupled to said housing and can be actuated to bend the surgical instrument to a position along said scale to allow the operator to select a bend angle of the surgical instrument; and, an adjustable stop that limits the bend angle of the surgical instrument, said adjustable stop having one end that is adjacent to said scale and which engages the surgical instrument to define the bend angle.

2. The apparatus as recited in claim 1, further comprising a handle that is coupled to said anvil.

3. The apparatus as recited in claim 1, wherein said adjustable stop includes a slot that receives a screw which is attached to said housing.

4. The apparatus as recited in claim 1, wherein said anvil is pivotally connected to said housing.

5. The apparatus as recited in claim 1, further comprising a die mounted to said housing, wherein the surgical instrument is bent about said die.

* * * * *